United States Patent
MacDonald et al.

(10) Patent No.: US 8,518,469 B2
(45) Date of Patent: Aug. 27, 2013

(54) POWDERED BEVERAGE COMPOSITION

(75) Inventors: Jane Lee MacDonald, Yorktown Heights, NY (US); Morgan Whitney Chase, Ossining, NY (US); Kieran Patrick Spelman, New City, NY (US)

(73) Assignee: Kraft Foods Group Brands LLC, Northfield, IL (US)

( * ) Notice: Subject to any disclaimer, the term of this patent is extended or adjusted under 35 U.S.C. 154(b) by 328 days.

(21) Appl. No.: 11/761,836

(22) Filed: Jun. 12, 2007

(65) Prior Publication Data

US 2008/0311265 A1   Dec. 18, 2008

(51) Int. Cl.
*A23L 2/00* (2006.01)

(52) U.S. Cl.
USPC .................................................... 426/590

(58) Field of Classification Search
USPC .................................................... 426/590
See application file for complete search history.

(56) References Cited

U.S. PATENT DOCUMENTS

| | | | |
|---|---|---|---|
| 5,219,598 A * | 6/1993 | Anderson et al. | 426/96 |
| 6,180,159 B1 * | 1/2001 | Villagran et al. | 426/590 |
| 6,248,390 B1 | 6/2001 | Stillman | |
| 2002/0127319 A1 | 9/2002 | Gare | |
| 2003/0059514 A1 * | 3/2003 | Villagran et al. | 426/590 |
| 2005/0003054 A1 * | 1/2005 | McCampbell | 426/321 |
| 2005/0106305 A1 * | 5/2005 | Abraham et al. | 426/590 |
| 2006/0099324 A1 * | 5/2006 | Aurio et al. | 426/656 |
| 2006/0228454 A1 * | 10/2006 | Ackilli et al. | 426/534 |
| 2006/0286260 A1 | 12/2006 | Nayak et al. | |

FOREIGN PATENT DOCUMENTS

| | | |
|---|---|---|
| AU | 2006100120 A4 * | 4/2006 |
| CN | 1457704 A | 11/2003 |
| JP | 11123053 A | 5/1999 |
| WO | 03/090558 A1 | 11/2003 |
| WO | 2008/066308 A1 | 6/2008 |

OTHER PUBLICATIONS

Dow Corning Product Information Brochure for AF Emulsion. 1999 (no month).*
Rainbow Light Food-Based Protein Energizer Supplement Powder—Vanilla Energy Shake, Rainbow Light Nutritional Systems, Inc., Apr. 10, 2006, Copyright 2007, Productscan Online, www.productscan.com, 1 page.
So Good Soy Beverage—Original; Fat Free Vanilla; Original No Sugar Added, Soya World Inc., Dec. 8, 2005, Copyright 2007, Productscan Online, www.productscan.com, 1 page.
Lifeway Slim6 Low Carb Lowfat Kefir Smoothie—Plain; Strawberries n' Cream; Mixed Berry; Tropical Fruit; Banana Strawberry, Lifeway Foods, Inc., Sep. 26, 2005, Copyright 2007, Productscan Online, www.productscan.com, 2 pages.
Zoic Low Carb! Protein Nutrition Drink—French Vanilla; Belgian Chocolate, LifeForce Labs, LLC, Jul. 12, 2004, Copyright 2007, Productscan Online, www.productscan.com, 2 pages.
Rainbow Light Food-Based Protein Energizer Supplement Powder—Creamy Vanilla Flavor; Chocolate, Rainbow Light Nutritional Systems Inc., Jun. 14, 2004, Copyright 2007, Productscan Online, www.productscan.com, 2 pages.
T. J. Skatrud et al., Designing new fermented foods, Food Engineering, 53(7), 80-82, 1981, Food Science and Technology Abstracts, 1 page Abstract.
R. Wyers, Nutritional concepts, World of Food Ingredients, December, 54-58, Foodline Science, 1 page Abstract.

* cited by examiner

*Primary Examiner* — D. Lawrence Tarazano
*Assistant Examiner* — Jenna A Watts
(74) *Attorney, Agent, or Firm* — Fitch, Even, Tabin & Flannery LLP

(57) ABSTRACT

The invention relates to a cold water soluble, low calorie, low net carbohydrate powdered beverage composition containing protein and fiber suitable for reconstitution with water or aqueous based liquids. More specifically, the present invention relates to a cold water soluble, low calorie, low net carbohydrate powdered beverage composition comprising (1) a protein component, (2) a soluble fiber component, and (3) an optional high intensity sweetener component, wherein the soluble fiber component increases the flowability and cold water solubility of the powdered beverage composition.

23 Claims, No Drawings

POWDERED BEVERAGE COMPOSITION

FIELD OF THE INVENTION

The present invention relates to a cold water soluble, low calorie, low net carbohydrate powdered beverage composition containing protein and fiber suitable for reconstitution with water or aqueous liquid. More specifically, the present invention relates to a cold water soluble, low calorie, low net carbohydrate powdered beverage composition comprising (1) a protein component, (2) a soluble fiber component, and (3) an optional high intensity sweetener component, wherein the powdered beverage composition is flowable and easily soluble in cold water. The present invention also relates to beverages prepared with the cold water soluble, low calorie, low net carbohydrate powdered beverage composition.

BACKGROUND

Obesity has been recognized as a significant and growing health problem on a global scale. Efforts to address this problem include, for example, surgical intervention, lifestyle changes, diet plans, exercise plans, nutritional supplements, satiety-inducing compositions, and many others. Although these efforts can be successful in the short term, long term success rates are generally much lower, resulting in the so-called "yo-yo" effect where weight is lost, then gained (often more than that lost), in a repeating cycle. Thus additional tools are needed, especially ones easy to implement and easy to use and which are convenient.

Protein-, fiber-, and fat-containing beverages are available. It has been found that such compositions can induce a feeling of satiety, thereby reducing the hungry feeling and assisting in reducing calorie intake from other foods. Such beverages are available in powdered forms for reconstitution in liquid by the consumer at the time of consumption and in ready-to-drink forms. Unfortunately, the commercial available beverage products suffer a number of drawbacks. Both powdered and ready-to-drink beverage products tend to possess poor, or at least less than desired, taste, mouthfeel, or other organoleptic properties. Powdered compositions, although more convenient to carry around than ready-to-drink beverage, are often difficult to reconstitute and generally require mechanical means, such as power blenders or mixers to solubilize the protein and other ingredients. This, of course, significantly reduces the convenience of the product. If such mechanical means are not used, incomplete solubility results in significantly reduced organoleptic properties, including, for example, grittiness. Additionally, such powdered compositions often use carriers such as sugar, maltodextrin, and the like, thereby significantly increasing the calorie content (generally 100 calories (total or digestible) or more per single serving) as well as the bulkiness of the product. Consumers are often willing to accept such products with their inherent defects because of the nutritional benefit expected from the product.

Of course, it would be desirable to provide powdered compositions from which beverages can be prepared and which provide the desired nutritional benefits, improved taste, mouthfeel, or other organoleptic properties. Ideally, such powdered compositions are also are easily prepared without mechanical means, and are low calorie, fat free, and contain low levels of net carbohydrates. Of course, the beverage prepared from the powdered composition should also have the desired effect of satiety. The present invention provides such compositions.

SUMMARY OF THE INVENTION

The present invention relates to a cold water soluble, low calorie, low net carbohydrate powdered beverage composition containing protein and fiber suitable for reconstitution with water or aqueous based liquids. The powdered beverage composition comprises (1) a protein component, (2) a soluble fiber component, and (3) an optional high intensity sweetener component. The powdered beverage composition has good flowability and cold water solubility so that the beverage can be prepared without the use of blenders or mixers in cold water. A single serving of the powdered beverage composition, as well as a single serving of beverage prepared using water, provides less than about 50 calories, about 1 to about 6 grams protein, about 2 to about 10 grams soluble fiber, less than about 2 grams net carbohydrates, and less than about 0.5 grams fat. For purposes of this invention, "net carbohydrate" is defined as total carbohydrates minus fiber. Preferably the powdered beverage compositions contain less than about 0.5 g fat, preferably less than about 0.2 g fat, and more preferably essentially no fat, per single serving. The powdered beverage compositions of the present invention can be provided in easy to carry single serving packaging (i.e., single serve "on the go" stick or tube packages) and can be designed to be reconstituted in commonly available bottled water containers (e.g., 500 ml sized bottled water). Due to the cold water solubility of the powdered beverage composition, the dry composition can simply be added to chilled water and shaken by hand to prepare the beverage. This reconstitution can be effected by simply pouring the powdered composition into the chilled water bottle, replacing the cap, and shaking the water bottle with a back and forth motion by hand.

The present invention also provides a powdered beverage composition suitable for reconstitution in water or aqueous based liquid to form a protein-containing and fiber-containing beverage, said powdered beverage composition comprising (1) a protein component, (2) a soluble fiber component, and (3) an optional high intensity sweetener component; wherein the soluble fiber component increases the flowability and cold water solubility of the powdered beverage composition; wherein a single serving size of the powdered beverage composition provides less than about 50 calories, about 1 to about 6 g protein, about 2 to about 10 g soluble fiber, less than about 0.5 g fat, and less than about 2 g net carbohydrates when reconstituted with water or aqueous based liquid to form a single serving of the protein-containing and fiber-containing beverage.

The present powdered beverage composition, when reconstituted with water or other aqueous fluids, provides a beverage which can induce a feeling of satiety, thereby reducing the feelings associated with hunger and the hunger-based desire for food. This beverage can be consumed before a meal, during a meal, or between meals, thereby reducing the craving for food and thus hopefully reducing the ingestion of higher calorie, higher fat, and/or less nutritionally balanced food or beverage products. Since the resulting beverage prepared with water is low caloric, the consumption of the beverage can reduce calorie intake without supplying significant amounts of its own calories. The resulting beverage can be a helpful tool in the fight against overeating and weight gain, including obesity. Testing has shown a feeling of satiety remains up to about two hours after consuming a single serving of the beverage obtained from the powdered beverage composition and water. Due to its low calorie content as well as its fat free and low net carbohydrate status, the resulting beverage can be an useful part and/or supplement to the dieting plans of many consumers whether they are dieting on their own or using one of the many diet plans commercially available.

DETAILED DESCRIPTION

A cold water soluble, low calorie, low net carbohydrate powdered beverage composition containing protein and fiber suitable for reconstitution with water or aqueous based liquids is provided. The powdered beverage composition comprises (1) a protein component, (2) a soluble fiber component, and (3) an optional high intensity sweetener component. The powdered beverage composition has good flowability and cold water solubility so that the beverage can be prepared without the use of blenders or mixers in cold water. A single serving of the powdered beverage composition, as well as a single serving of beverage prepared using water, provides less than about 50 calories, about 1 to about 6 grams protein, about 2 to about 10 grams soluble fiber, less than about 2 grams net carbohydrates, and less than about 0.5 grams fat. The powdered beverage compositions of the present invention can be provided in easy to carry single serving packaging (i.e., single serve "on the go" stick packages) and can be designed to be reconstituted in commonly available bottled water containers (e.g., 500 ml sized bottled water). Due to the cold water solubility of the powdered beverage composition, the dry composition can simply be added to chilled water and shaken by hand to prepare the beverage. This reconstitution can be effected by simply pouring the powdered composition into the chilled water bottle, replacing the cap, and shaking the water bottle with a back and forth motion by hand.

In one embodiment, comprises per single serving size (1) about 1 to 6 grams protein component, (2) about 2 to 10 grams soluble fiber component, (3) 0 to about 5 grams organic acid, (4) 0 to about 1.8 grams high intensity sweetener component, (5) 0 to about 0.3 grams anticaking agent, (6) 0 to about 0.5 grams of at least one carbonate salt from the group consisting of calcium carbonate, sodium bicarbonate, and potassium bicarbonate, (7) 0 to about 1 grams of flow agent, (8) 0 to about 0.03 grams antifoam agent, and (9) 0 to 1 gram of flavorants and colorants; wherein the soluble fiber component increases the flowability and cold water solubility of the powdered beverage composition; wherein the single serving size of the powdered beverage composition provides less than about 50 calories, about 1 to about 6 g protein, about 2 to about 10 grams soluble fiber, less than about 0.5 grams fat, and less than about 2 grams net carbohydrates when reconstituted with 500 ml water or aqueous based liquid to form a single serving of the protein-containing and fiber-containing beverage.

In another embodiment, the powdered beverage composition comprises per single serving size (1) about 2 to 5 grams protein component, (2) about 3 to 7 grams soluble fiber component, (3) about 1 to about 3 grams organic acid, (4) 0.1 to about 0.6 grams high intensity sweetener component, (5) about 0.01 to about 0.1 grams anticaking agent, (6) 0.01 to about 0.1 grams of at one least carbonate salt from the group consisting of calcium carbonate, sodium bicarbonate, and potassium bicarbonate, (7) about 0.04 to about 0.12 grams of flow agent, (8) about 0.01 to about 0.03 grams antifoam agent, and (9) about 0.2 to 0.5 grams of flavorants and colorants; wherein the soluble fiber component increases the flowability and cold water solubility of the powdered beverage composition; wherein the single serving size of the powdered beverage composition provides less than about 50 calories, about 1 to about 6 g protein, about 2 to about 10 grams soluble fiber, less than about 0.5 grams fat, and less than about 2 grams net carbohydrates when reconstituted with 500 ml water or aqueous based liquid to form a single serving of the protein-containing and fiber-containing beverage.

For purposes of this invention, flowability is defined as the ability of the powdered composition, when contained in suitable single serving packaging (e.g., single serving stick, tube, or cylinder packaging), to be simply and easily poured into a water container without significant material remaining in the packaging. For purposes of this invention, cold water solubility is generally to be evaluated at about 48 to about 52° F.; in many cases, however, the composition will be soluble at lower temperatures. And although the powdered beverage composition are designed for use with cold water, of course, the consumer may make the beverage using colder or warmer water.

Generally, the dry beverage compositions of the present invention contain the following ingredients in the listed amounts for a single serving:

| Ingredient | Range (g) | Preferred Range (g) |
| --- | --- | --- |
| Protein | 1-6 | 2-5 |
| Soluble Fiber | 2-10 | 3-7 |
| Organic Acid | 0-5 | 1-2.5 |
| High Intensity Sweetener | 0-1.8 | 0.1-0.6 |
| Anticaking Agent | 0-0.3 | 0.01-0.05 |
| Carbonate Salt | 0-0.5 | 0.05-0.02 |
| Flow Agent | 0-1.0 | 0.04-0.12 |
| Antifoam | 0-0.03 | 0.01-0.025 |
| Colorants/Flavorants | 0-1.0 | 0.2-0.5 |

The above table illustrates formulations suitable for single serving sizes (generally about 3 to about 25 g total and preferably about 10 to about 15 g total) that can be used to make a single serving of beverage using about 500 ml water. Preferably a single serving is packaged in its own package and is ideally suited for the consumer who would like to carry them on their person; to use, they could simply stop at any convenience or other store that sells bottled water, buy the appropriate sized bottled water (generally about 500 ml), pour the contents of the single serve pack into the bottled water, replace the cap, and shake by hand. Of course, other single serving sizes can be provided for other sized bottles. Or the product could be in the form of multiple serving sizes or even bulk sizes.

Generally, the weight ratio of protein to soluble fiber is in the range of about 1:3 to about 3:10, and more preferably in the range of about 3:5 to about 3:10. Such relative levels of protein and soluble fiber provide good satiety properties. Thus, the compositions of this invention provide useful tools for weight loss programs and/or maintaining weight loss since they provide a low calorie beverage which can reduce the feelings of hunger for several hours. Thus, they can be used between meals to reduce the desire to consume snacks or other high calorie foods. They can be used shortly before meals, or even during meals, to reduce the feeling of hunger so smaller portions can be consumed while still providing the feeling of being satisfied.

Suitable proteins include, for example, whey protein, soy protein, milk protein, vegetable proteins, starch-based proteins, and the like as well as mixtures thereof. Preferably the protein used in the present invention is a high quality protein such as, for example, whey protein, soy protein, milk protein, and the like as well as mixtures thereof. For purposes of this invention, high quality protein is protein which provides an essentially complete profile of the amino acids necessary in the human diet. The protein preferably is in the form of a water soluble powder; it may be concentrated, hydrolyzed, isolated, instantized, and/or agglomerated. The preferred high quality protein is whey protein, with Instantized BiPro® (instantized whey protein isolate prepared from fresh sweet dairy whey that is concentrated and spray dried; Davisco Foods International, Le Sueur, Minn.) being most preferred.

The soluble fiber includes inulin (e.g., Beneo™ GR; (granulated inulin obtained from chicory root; ORAFTI Group, Belgium), modified corn and wheat dextrins (e.g., Nutriose®; Roquette, France; Fibersol-2®; Matsutani Chemical Industry Co.), fructo-oligosaccharide, polydextrose, Benefiber® (Novartis Consumer Health, Inc.), acacia gum, pectin, guar gum, locust bean gum, hemicelluloses, beta glucan, and the like as well as mixtures thereof. Although not wishing to be limited by theory, it appears that the incorporation of the soluble fiber improves the flowability and solubility of the composition in cold water. The preferred soluble fiber is inulin, with Beneo™ GR being the most preferred.

Preferably the powdered beverage composition also contains an organic acid in an amount effective to provide the desired pH in the reconstituted beverage. Typically, the pH may be in the range of about 2 to about 8, with about 2.5 to about 4.2 being preferred. Suitable organic acids include citric acid, malic acid, tartaric acid, lactic acid, adipic acid, fumaric acid, and the like as well as mixtures thereof. Preferably citric acid is used. The organic acid may also act as a flavorant.

Preferably the powdered beverage composition also contains a high intensity sweetener having low or essentially no calorie content. Suitable sweeteners include aspartame, sucralose, neotame, acesulfame potassium, cyclamate, stevia, Lo Han Guo, Brazzein, monatin, saccharin, thaumatin, alitame, neohespederin dihydrochalcone, sugar alcohols, and the like as well as mixtures thereof in an amount effective to provide the desired level of sweetness. Aspartame is the preferred high intensity sweetener. In order to maintain the low calorie content of the present invention (i.e., less than about 50 calories per serving, preferably less than about 40 calories per serving, and preferably about 25 to about 35 calories per serving), sugar should not be included in the formulation. For purposes of this invention, the calorie content refers to digestible or available calories which, in some cases, may be lower that total calories.

Preferably the powdered beverage composition also contains an anticaking agent to help maintain the flowability of the powdered beverage composition. Suitable anticaking agents include magnesium oxide, tricalcium phosphate, dicalcium phosphate, monocalcium phosphate, and the like as well as mixtures thereof. Magnesium oxide is the preferred anticaking agent for use in this invention. Although not wishing to be limited by theory, it is thought that the anticaking agent effectively absorbs any moisture that may be introduced with the ingredients or otherwise enter the package, thereby maintaining the flowability of the powdered beverage composition.

Preferably the powdered beverage composition also contains a carbonate salt selected from the group consisting of calcium carbonate, sodium carbonate, potassium carbonate, and the like as well as mixtures thereof. Preferably a mixture of calcium carbonate, sodium carbonate, and potassium carbonate is used; even more preferably a mixture containing calcium carbonate, sodium carbonate, and potassium carbonate in a 2:2:1 weight ratio is used. Although not wishing to be limited by theory, it is thought that the carbonate salts, when added to the reconstituting water in the presence of organic acids, will react with the organic acids to form a small amount of gas which helps to disperse and break up the powdered particles so they can more easily be dispersed and dissolved in the aqueous medium.

Preferably the powdered beverage composition also contains a flow agent to help maintain the flowability. Generally silicate based flow agents are preferred with FloGard® SP (PPG Co.) being most preferred.

Preferably the powdered beverage composition also contains a antifoaming agent to prevent or significantly reduce foam formation when the powdered beverage composition is reconstituted in the aqueous medium. Silicone based (liquid or solid) antifoaming agents and surface active surfactants (e.g., fatty acids, fatty acid esters, fatty alcohols, phospholipids, monoglycerides, diglycerides, and the like) can be used. One especially preferred antifoaming agent is 1920 Powdered Antifoam from Dow Corning Corp. (Midland, Mich.).

Preferably the powdered beverage composition also contains effective amounts of food grade colorants and flavorants to provide the desired color and favoring. The flavorants include various fruit flavors, tea, coffee, vanilla, chocolate, dairy, and the like.

Of course, the powdered beverage compositions of this invention may contain other optional ingredients so long as the do not adversely affect the desirable properties. Thus, for example, the composition could be fortified with mineral, nutrients, and the like.

The powdered beverage compositions of the present invention may be prepared using conventional powder handling methods such as, for example, dry mixing, agglomeration, co-drying ingredients using extrusion, drum drying, freeze drying, or spray drying and the like. It is generally preferred that about half the fiber, all other ingredients (except protein), and the remaining fiber are combined in that order, and mixed until evenly distributed (generally about 5 to 10 minutes on a laboratory scale); the protein is then added and mixing continues until a homogenous powder (generally about 3 to about 5 minutes on a laboratory scale) is obtained in order to reduce the exposure of protein to shear. They readily disperse/dissolve in cold water using only hand mixing.

The following examples describe and illustrate the processes and products of the invention. These examples are intended to be merely illustrative of the present invention, and not limiting thereof in either scope or spirit. Unless indicated otherwise, all percentages and ratios are by weight. Those skilled in the art will readily understand that variations of the materials, conditions, and processes described in these examples can be used. All references cited herein are incorporated by reference.

EXAMPLE 1

A powdered beverage composition was prepared using the following formulation (based on a single serving to be reconstituted in 500 ml water):

| Ingredient | Tradename | Amount (g) |
| --- | --- | --- |
| Whey Protein | Instantized BiPro ® (Davisco Foods) | 3.3 |
| Inulin | Beneo ™ GR (ORAFTI Group) | 5.6 |
| Citric Acid | — | 1.4 |
| Aspartame | — | 0.4 |
| Magnesium Oxide | — | 0.03 |
| Calcium Carbonate | — | 0.039 |
| Sodium Bicarbonate | — | 0.039 |
| Potassium Bicarbonate | — | 0.019 |

-continued

| Ingredient | Tradename | Amount (g) |
|---|---|---|
| Silica | FloGard ® SP (PPG Co.) | 0.06 |
| Silicone | 1920 Powdered Antifoam (Dow Corning ®) | 0.025 |
| Colorants/Flavorants | — | 0.26 |

The ingredients were dry blended. The total weight of a single serving formulation was about 11.09 g. The composition was flowable and could be easily dissolved in cold water (500 ml) with hand shaking (i.e., in a capped bottle with headspace to allow better mixing using about 20 vigorous shakes by hand).

When reconstituted in 500 ml cold water (about 48 to about 52° F.), the resulting beverage contained about 30 calories (essentially all of which are digestible or available), about 3 grams protein, about 5 grams soluble fiber, less than about 2 grams net carbohydrates, and essentially zero fat. The resulting beverage had good organoleptic properties with no evidence of grittiness.

A test panel consumed a single serving of the reconstituted beverage and then was asked various satiety questions about every 15 minutes. The time to return to pre-ingestion satiety was less than about 2 hours.

EXAMPLE 2

A powdered beverage composition was prepared using the following formulation:

| Ingredient | Tradename | Amount (g) |
|---|---|---|
| Whey Protein | Instantized BiPro ® (Davisco) Foods | 3.3 |
| Modified Corn Dextrin | Fibersol-2 ® (Matsutani Chemical) | 5.8 |
| Citric Acid | — | 1.24 |
| Malic Acid | — | 0.088 |
| Aspartame | — | 0.15 |
| Colorants/Flavorants | — | 0.26 |

When reconstituted in 500 ml cold water, the resulting beverage had a clean taste and good organoleptic properties with no evidence of grittiness. A single serving has about 35 total calories of which about 25 calories are digestible.

EXAMPLE 3

A powdered beverage composition was prepared using the following formulation:

| Ingredient | Tradename | Amount (g) |
|---|---|---|
| Whey Protein | Instantized BiPro ® (Davisco) Foods | 5.4 |
| Modified Corn Dextrin | Fibersol-2 ® (Matsutani Chemical) | 11.7 |
| Citric Acid | — | 1.24 |
| Malic Acid | — | 0.088 |
| Aspartame | — | 0.15 |
| Colorants/Flavorants | — | 0.26 |

When reconstituted in 500 ml cold water, the resulting beverage had a clean taste and good organoleptic properties with no evidence of grittiness. A single serving has about 70 total calories of which about 45 calories are digestible or available.

What is claimed is:

1. A powdered beverage composition suitable for being added to water or aqueous based liquid to form a protein-containing and fiber-containing beverage, said powdered beverage composition comprising (1) agglomerated protein, the agglomerated protein selected from the group consisting of whey protein, milk protein, and mixtures thereof, (2) a soluble fiber component, and (3) an optional high intensity sweetener component; the soluble fiber component present in an amount about 1.6 times to about 3.3 times greater by weight than the agglomerated protein; and the powdered beverage composition is soluble in water having a temperature below about 52° F. by using hand mixing; wherein the soluble fiber component increases the flowability and cold water solubility of the powdered beverage composition; and wherein a single serving size of about 3 to about 25 g of the powdered beverage composition has less than about 50 calories, about 1 to about 6 g protein, about 2 to about 10 g soluble fiber, less than about 0.5 g fat, and less than about 2 g net carbohydrates.

2. The powdered beverage composition of claim 1, wherein the soluble fiber component is inulin, fructo-oligosaccharide, polydextrose, modified corn dextrins, modified wheat dextrins, acacia gum, pectin, guar gum, locust bean gum, hemicelluloses, beta glucan, soluble corn fibers, soluble wheat fibers, or mixtures thereof.

3. The powdered beverage composition of claim 1, wherein the agglomerated protein is whey protein and the soluble fiber component is inulin.

4. The powdered beverage composition of claim 1, wherein the agglomerated protein is whey protein and the soluble fiber component is modified corn dextrins or modified wheat dextrins.

5. The powdered beverage composition of claim 1, wherein the powdered beverage composition provides less than about 40 calories, about 2 to about 5 g protein, about 3 to about 7 g soluble fiber, less than about 0.2 g fat, and less than about 2 g net carbohydrates.

6. The powdered beverage composition of claim 2, wherein the powdered beverage composition provides less than about 40 calories, about 2 to about 5 g protein, about 3 to about 7 g soluble fiber, less than about 0.2 g fat, and less than about 2 g net carbohydrates.

7. The powdered beverage composition of claim 3, wherein the powdered beverage composition provides less than about 40 calories, about 2 to about 5 g protein, about 3 to about 7 g soluble fiber, less than about 0.2 g fat, and less than about 2 g net carbohydrates.

8. The powdered beverage composition of claim 4, wherein the powdered beverage composition provides less than about 40 calories, about 2 to about 5 g protein, about 3 to about 7 g soluble fiber, less than about 0.2 g fat, and less than about 2 g net carbohydrates.

9. A powdered beverage composition suitable for being added to water or aqueous based liquid to form a protein-containing and fiber-containing beverage, said powdered beverage composition comprising (1) about 1 to 6 grams agglomerated protein, the agglomerated protein selected from the group consisting of whey protein, milk protein, and mixtures thereof, (2) about 2 to 10 grams soluble fiber component, (3) 0 to about 5 grams organic acid, (4) 0 to about 1.8 grams high intensity sweetener component, (5) 0 to about 0.3 grams anticaking agent, (6) 0 to about 0.5 grams of at least one carbonate salt from the group consisting of calcium carbonate, sodium bicarbonate, and potassium bicarbonate, (7) 0 to about 1 grams of flow agent, (8) 0 to about 0.03 grams antifoam agent, and (9) 0 to 1 gram of flavorants and colorants; the soluble fiber component present in an amount about 1.6 times to about 3.3 times greater by weight than the agglomerated protein; and the powdered beverage composition is soluble in water having a temperature below about 52° F. by using hand mixing; wherein the soluble fiber component increases the flowability and cold water solubility of the powdered beverage composition; and wherein a single serving size of about 3 to about 25 g of the powdered beverage composition has than about 50 calories, about 1 to about 6 g protein, about 2 to about 10 grams soluble fiber, less than about 0.5 grams fat, and less than about 2 grams net carbohydrates.

10. The powdered beverage composition of claim 9, wherein the soluble fiber component is selected from the group consisting of inulin, fructo-oligosaccharide, polydextrose, modified corn dextrins, modified wheat dextrins, acacia gum, pectin, guar gum, locust bean gum, hemicelluloses, beta glucan, soluble corn fibers, soluble wheat fibers, and mixtures thereof; wherein the organic acid is selected from the group consisting of citric acid, malic acid, tartaric acid, lactic acid, adipic acid, fumaric acid, and mixtures thereof; wherein the high intensity sweetener component selected from the group consisting of aspartame, sucralose, neotame, acesulfame potassium, cyclamate, stevia, and mixtures thereof; wherein the anticaking agent is selected from the group consisting of magnesium oxide, tricalcium phosphate, dicalcium phosphate, monocalcium phosphate, and mixtures thereof; wherein the flow agent is a silicate; and wherein the antifoam agent selected from the group consisting of silicone based antifoaming agents and surface active surfactants.

11. The powdered beverage composition of claim 9, wherein the agglomerated protein is whey protein; wherein the soluble fiber component is inulin, modified corn dextrins, or modified wheat dextrins; wherein the organic acid is citric acid, malic acid, or mixtures thereof; wherein the high intensity sweetener component is aspartame; wherein the anticaking agent is magnesium oxide; wherein the carbonate salt is a mixture of calcium carbonate, sodium bicarbonate, and potassium bicarbonate; wherein the flow agent is a silicate; and wherein the antifoam agent is a silicone based antifoaming agent.

12. The powdered beverage composition of claim 9, wherein the powdered beverage composition provides less than about 40 calories, about 2 to about 5 g protein, about 3 to about 7 g soluble fiber, less than about 0.2 g fat, and less than about 2 g net carbohydrates.

13. The powdered beverage composition of claim 10, wherein the powdered beverage composition provides less than about 40 calories, about 2 to about 5 g protein, about 3 to about 7 g soluble fiber, less than about 0.2 g fat, and less than about 2 g net carbohydrates.

14. The powdered beverage composition of claim 11, wherein the powdered beverage composition provides less than about 40 calories, about 2 to about 5 g protein, about 3 to about 7 g soluble fiber, less than about 0.2 g fat, and less than about 2 g net carbohydrates.

15. A powdered beverage composition suitable for being added to water or aqueous based liquid to form a protein-containing and fiber-containing beverage, said powdered beverage composition comprising (1) about 2 to 5 grams agglomerated protein, the agglomerated protein selected from the group consisting of whey protein, milk protein, and mixtures thereof, (2) about 3 to 7 grams soluble fiber component, (3) about 1 to about 3 grams organic acid, (4) 0.1 to about 0.6 grams high intensity sweetener component, (5) about 0.01 to about 0.1 grams anticaking agent, (6) 0.01 to about 0.1 grams of at one least carbonate salt from the group consisting of calcium carbonate, sodium bicarbonate, and potassium bicarbonate, (7) about 0.04 to about 0.12 grams of flow agent, (8) about 0.01 to about 0.03 grams antifoam agent, and (9) about 0.2 to 0.5 grams of flavorants and colorants; the soluble fiber component present in an amount about 1.6 times to about 3.3 times greater by weight than the agglomerated protein; and the powdered beverage composition is soluble in water having a temperature below about 52° F. by using hand mixing; wherein the soluble fiber component increases the flowability and cold water solubility of the powdered beverage composition; and wherein a single serving size of about 10 to about 15 g of the powdered beverage composition has less than about 50 calories, about 2 to about 5 g protein, about 3 to about 7 grams soluble fiber, less than about 0.5 grams fat, and less than about 2 grams net carbohydrates.

16. The powdered beverage composition of claim 15, wherein the soluble fiber component is selected from the group consisting of inulin, nutriose, fructo-oligosaccharide, polydextrose, modified corn dextrins, modified wheat dextrins, acacia gum, pectin, guar gum, locust bean gum, hemicelluloses, beta glucan, soluble corn fibers, soluble wheat fibers, and mixtures thereof; wherein the organic acid is selected from the group consisting of citric acid, malic acid, tartaric acid, lactic acid, adipic acid, fumaric acid, and mixtures thereof; wherein the high intensity sweetener component selected from the group consisting of aspartame, sucralose, neotame, acesulfame potassium, cyclamate, stevia, and mixtures thereof; wherein the anticaking agent is selected from the group consisting of magnesium oxide, tricalcium phosphate, dicalcium phosphate, monocalcium phosphate, and mixtures thereof; wherein the flow agent is a silicate; and wherein the antifoam agent selected from the group consisting of silicone based antifoaming agents and surface active surfactants.

17. The powdered beverage composition of claim 15, wherein the agglomerated protein is whey protein; wherein the soluble fiber component is inulin, modified corn dextrins, or modified wheat dextrins; wherein the organic acid is citric acid, malic acid, or mixtures thereof; wherein the high intensity sweetener component is aspartame; wherein the anticaking agent is magnesium oxide; wherein the carbonate salt is a mixture of calcium carbonate, sodium bicarbonate, and potassium bicarbonate; wherein the flow agent is a silicate; and wherein the antifoam agent is a silicone based antifoaming agent.

18. The powdered beverage composition of claim 15, wherein the powdered beverage composition provides less than about 40 calories, about 2 to about 5 g protein, about 3 to about 7 g soluble fiber, less than about 0.2 g fat, and less than about 2 g net carbohydrates.

19. The powdered beverage composition of claim 16, wherein the powdered beverage composition provides less than about 40 calories, about 2 to about 5 g protein, about 3 to about 7 g soluble fiber, less than about 0.2 g fat, and less than about 2 g net carbohydrates.

20. The powdered beverage composition of claim 17, wherein the powdered beverage composition provides less than about 40 calories, about 2 to about 5 g protein, about 3 to about 7 g soluble fiber, less than about 0.2 g fat, and less than about 2 g net carbohydrates when reconstituted with water or aqueous based liquid.

21. The powdered beverage composition of claim 1, wherein the weight ratio of the agglomerated protein to the soluble fiber component is in the range of about 1:3 to about 3:10.

22. The powdered beverage composition of claim 9, wherein the weight ratio of the agglomerated protein to the soluble fiber component is in the range of about 1:3 to about 3:10.

23. The powdered beverage composition of claim 15, wherein the weight ratio of the agglomerated protein to the soluble fiber component is in the range of about 1:3 to about 3:10.

* * * * *

UNITED STATES PATENT AND TRADEMARK OFFICE
CERTIFICATE OF CORRECTION

| | | |
|---|---|---|
| PATENT NO. | : 8,518,469 B2 | Page 1 of 1 |
| APPLICATION NO. | : 11/761836 | |
| DATED | : August 27, 2013 | |
| INVENTOR(S) | : MacDonald | |

It is certified that error appears in the above-identified patent and that said Letters Patent is hereby corrected as shown below:

IN THE CLAIMS:
Column 9, line 9, Claim 9, after "has" insert --less--.
Column 9, line 67, Claim 15, delete "one least" and insert --least one-- therefor.

Signed and Sealed this
Third Day of June, 2014

Michelle K. Lee
*Deputy Director of the United States Patent and Trademark Office*